US00PP31444P2

(12) United States Plant Patent
Olsen

(10) Patent No.: US PP31,444 P2
(45) Date of Patent: Feb. 18, 2020

(54) PEAR TREE NAMED 'OLSEN BOSC'

(50) Latin Name: ***Pyrus communis* L.**
Varietal Denomination: Olsen Bosc

(71) Applicant: David Olsen, Zillah, WA (US)

(72) Inventor: David Olsen, Zillah, WA (US)

( * ) Notice: Subject to any disclaimer, the term of this patent is extended or adjusted under 35 U.S.C. 154(b) by 0 days.

(21) Appl. No.: 16/350,847

(22) Filed: Jan. 22, 2019

(51) Int. Cl.
*A01H 5/08* (2018.01)
*A01H 6/74* (2018.01)

(52) U.S. Cl.
USPC ..... Plt./176
CPC ..... *A01H 6/7481* (2018.05)

(58) Field of Classification Search
USPC ..... Plt./176
See application file for complete search history.

*Primary Examiner* — Anne Marie Grunberg
(74) *Attorney, Agent, or Firm* — Michelle Bos Legal LLC

(57) ABSTRACT

The 'Olsen Bosc' pear tree, a mutation of 'Bosc', is notable for its distinctive fruit. Profound russeting on substantially the entire surface of the skin gives 'Olsen Bosc' pears a distinctive bronze appearance.

3 Drawing Sheets

Latin name: *Pyrus communis* L.
Variety denomination: 'Olsen Bosc'.

BACKGROUND OF THE VARIETY

'Olsen Bosc' is a new and distinct variety of pear tree (*Pyrus communis* L.) discovered as a limb mutation of a 'Bosc' pear tree (not patented) growing in a cultivated pear orchard near Zillah, Wash. in 2000. Fruit on the mutated limb was observed to be smoother and more russeted than fruit found elsewhere on the tree. After several years of observation, buds from the limb mutation were asexually propagated by grafting at a fruit tree nursery near Quincy, Wash. in 2007. 'Olsen Bosc' has since been asexually reproduced and fruited through successive generations at Quincy, Wash., and has been observed to remain true to type.

BRIEF DESCRIPTION OF THE VARIETY

'Olsen Bosc' was first distinguished from the parent tree, and later selected for further observation and propagation, because of its distinctive fruit. The profound russeting on substantially all of the fruit surface gives the fruit a distinctive bronze appearance. 'Olsen Bosc' is also distinguished from similar variety 'Golden Russet Bosc' (U.S. Plant Pat. No. 5,243, expired). A comparison of the fruit of 'Olsen Bosc' to 'Golden Russet Bosc' is set forth in Table 1 below.

TABLE 1

Comparison of fruit of 'Olsen Bosc' to 'Golden Russet Bosc'

| | 'Olsen Bosc' | 'Golden Russet Bosc' |
|---|---|---|
| Amount of russet on skin | 95% to 100% | 40% to 60% |
| Texture of russet | Rougher, duller | Smoother, more shiny |
| Surface smoothness | Fewer bumps and protruberances | More bumps and protruberances |
| Fruit lenticels | More pronounced | Less pronounced |
| Fruit shape | Between pyriform and long pyriform | More toward long pyriform |
| Shape of calyx end | Flatter, with little to no crowning | Pronounced crowning |

TABLE 1-continued

Comparison of fruit of 'Olsen Bosc' to 'Golden Russet Bosc'

| | 'Olsen Bosc' | 'Golden Russet Bosc' |
|---|---|---|
| Flesh | Firmer and sweeter (16 °Brix); less acid | Less firm; less sweet (15.5 °Brix); slightly juicier |
| Stem diameter | 2.5 mm to 3 mm | 2.5 mm |

BRIEF DESCRIPTION OF THE PHOTOGRAPHS

DETAILED BOTANICAL DESCRIPTION OF THE VARIETY

Figure 1:
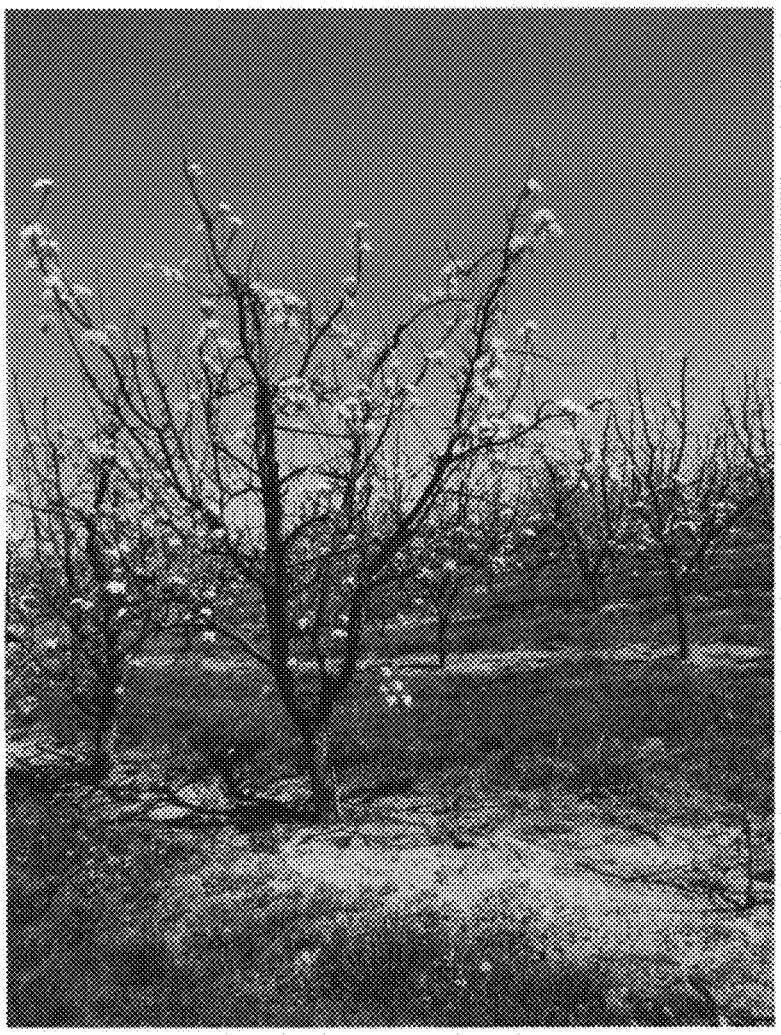
FIG. 1 is a photograph of a nine-year-old 'Olsen Bosc' tree taken in March 2018 near Zillah, Wash.
Figure 2:
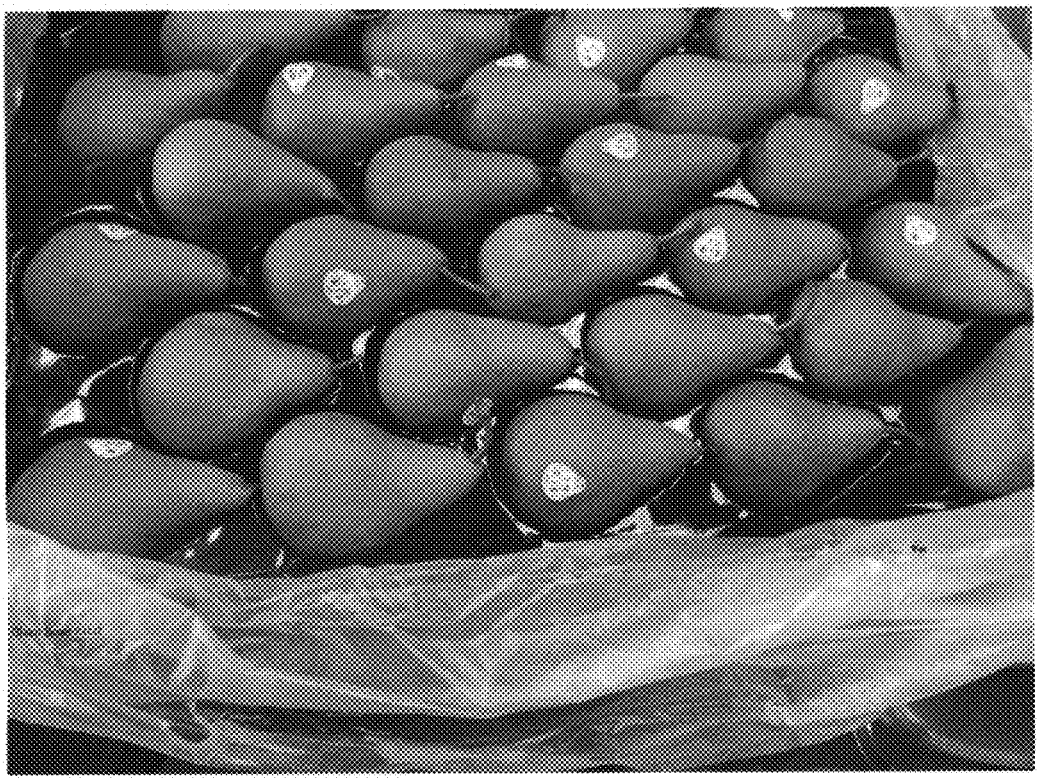
FIG. 2 is a photograph of fruit of 'Olsen Bosc'.
Figure 3:
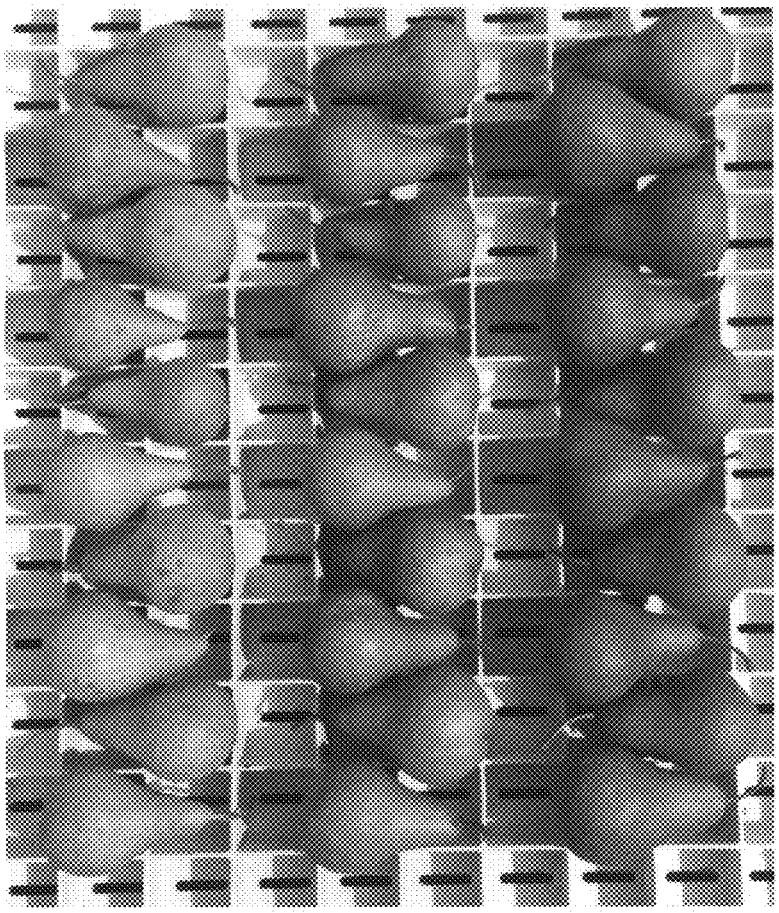
FIG. 3 is a photograph of standard 'Bosc' (left), 'Golden Russet Bosc' (center), and 'Olsen Bosc' (right) pears.

The following-detailed botanical description is based on observations made near Zillah, Wash. during the 2015 growing season (unless otherwise noted). The described trees were six years old, grown on 'Old Home x Farmingdale 97' rootstock (not patented). All colors are described according to the Munsell Book of Color. It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:

*Vigor*.—Highly vigorous, similar to 'Bosc'.
*Habit*.—Upright to spreading.
*Height*.—About 3.6 m to 5.5 m.
*Spread*.—About 3.0 m.

*Trunk diameter* (*at* 30 *cm above the graft*).—16 cm.
*Bark texture*.—Rough.
*Bark color*.—Gray 7.5 Y 7/2.
*Winter hardiness*.—Similar to 'Bosc'.

Branch (fruiting branches located at around 1 m above the graft union):
*Length*.—2.8 m.
*Diameter*.—7 cm to 11 cm.
*Crotch angle*.—90°.
*Bark color*.—Gray 7.5 Y 7/2.

One year old shoot:
*Length*.—18 cm to 50 cm.
*Color*.—Medium brown 7.5YR 4/4.
*Pubescence*.—None, glabrous.
*Thickness*.—8 mm to 12 mm.
*Internode length*.—4 cm to 7 cm.
*Pubescence*.—None, glabrous.
*Number of lenticels*.—4 to 10 per $cm^2$.
*Vegetative bud shape*.—Broad ovoid, typical of 'Bosc'.
*Vegetative bud color*.—Dark brown 7.5 YR 3/4.
*Position of vegetative buds in relation to shoot*.—Approximately 45°, typical of 'Bosc'.

Flower buds:
*Quantity per spur*.—2 to 4.
*Shape*.—Broad ovoid.
*Length*.—8 mm to 10 mm.
*Diameter*.—4 mm to 6 mm.
*Color*.—Light brown 7.5 YR 4/2.

Flowers:
*Diameter of fully open flower*.—30 mm to 40 mm.
*Depth of open flower*.—10 mm.
*Relative position of petal margin*.—Usually not touching, sometimes touching at base.
*Number per cluster*.—6 to 10.
*Date of first bloom*.—Mar. 23, 2015; Apr. 2, 2016.
*Date of full bloom*.—Mar. 28, 2015; Apr. 7, 2016.
*Pollination requirement*.—Pollinator required, similar to 'Bosc'.

Petals:
*Number per flower*.—5.
*Shape*.—Elongated.
*Length*.—18 mm to 20 mm.
*Width*.—10 mm.
*Margin*.—Smooth.
*Color of upper surface*.—White.
*Color of lower surface*.—White.

Pistils:
*Length*.—6 mm to 8 mm.
*Color*.—Yellow white 7.5 Y 9/2.

Stigma:
*Length*.—6 mm.
*Color*.—Yellow white 7.5 Y 9/2.

Style:
*Length*.—10 mm.
*Color*.—Yellow white 7.5 Y 9/2.

Ovary:
*Size*.—4 mm.
*Color*.—Light green 7.5 Y 6/6.

Anthers:
*Quantity*.—16 to 20 per flower.
*Length*.—1.5 mm.
*Presence of pollen*.—Present.
*Color of pollen*.—Yellow 7.5 Y 8.5/12.

Pedicel:
*Length*.—18 mm to 20 mm.
*Diameter*.—2 mm.
*Color*.—Light green 2.5 GY 7/6.

Sepals:
*Quantity*.—5 per flower.
*Length*.—5 mm.
*Width*.—2 mm.
*Shape*.—Ranging from linearly lanceolate to lanceolate with a wide base.
*Apex*.—Slightly indented.
*Margin*.—Smooth.
*Attitude in relation to corolla*.—Spreading.

Leaves:
*Shape*.—Ovate.
*Length*.—7 cm to 10 cm.
*Width*.—2 cm to 8 cm.
*Length/width ratio*.—Ranging from 1:1 to 3:1.
*Blade margin*.—Entire.
*Apex*.—Acute to accuminate.
*Base*.—Generally rounded; cuneate to obtuse.
*Color of upper surface*.—Dark green 10GY 3/4.
*Color of lower surface*.—Light green 10 GY 5/4.
*Attitude in relation to shoot*.—30° to 60°.
*Curvature of longitudinal axis*.—Downward, from 90° to 180° from the vertical shoot.

Petiole:
*Length*.—2.5 cm to 3.5 cm.
*Diameter*.—2 mm.
*Petiole color*.—Yellowish green 2.5 GY 8/6.
*Stipule color*.—Yellowish green 2.5 GY 8/6.
*Stipule shape*.—Spinose.
*Stipule length*.—8 mm to 13 mm.
*Stipule width*.—0.5 mm.
*Stipule apex*.—Sharply pointed.

Fruit:
*Quantity per cluster*.—2 to 4.
*Height*.—9.5 cm to 11 cm; average 10.2.
*Width*.—6.5 cm to 7.8 cm; average 7.0 cm.
*Ratio of height to width*.—10:7.
*Weight*.—216 g; similar to 'Golden Russet Bosc'.
*General shape in profile*.—Pyriform; less elongated than 'Golden Russet Bosc'.
*Position of maximum diameter*.—Lower third.
*Symmetry in longitudinal section*.—Asymetrical; more pronounced than 'Golden Russet Bosc'.
*Profile of sides*.—Concave.
*Skin texture*.—Russeted and dull.
*Background color of skin*.—Yellowish brown 7.5 YR 7/10.
*Area of over color of skin*.—95% to 100%.
*Intensity of over color of skin*.—Intense.
*Color of overcolor*.—Reddish brown 7.5 YR 5/6.
*Relative area of russet around eye basin*.—90% to 100%.
*Relative area of russet on cheeks*.—95% to 100%.
*Relative area of russet on stalk attachment*.—100%.
*Length of stalk*.—3 cm to 4 cm; average 3.4 cm.
*Diameter of stalk*.—2.5 mm to 3 mm.
*Curvature of stalk*.—Somewhat curved, typical of 'Bosc'.
*Attitude of stalk in relation to axis of fruit*.—Somewhat off-center, typical of 'Bosc'.
*Stalk color*.—Dark brown 7.5 YR 3/4.
*Depth of eye basin*.—4 mm.

*Width of eye basin.*—17 mm.
*Firmness of flesh.*—17 to 22; average 19 lbs. pressure.
*Flesh texture.*—Crisp and fine-grained.
*Aroma.*—Aromatic.
*Juiciness.*—Medium to juicy.
*Brix.*—16° Brix.
*Flesh color.*—Cream 7.5 Y 9/4, transluscent.

Seeds:
*Quantity per fruit.*—7.
*Shape.*—Obovate.
*Length.*—7 mm.
*Width.*—5 mm.
*Color.*—Dark brown 7.5 Y 2/2.

Harvest:
*Time for harvest.*—Sep. 2, 2015; Aug. 29, 2016.
*Time of maturity for consumption.*—5 to 10 days after harvest.
*Amount of fruit produced per* 200 *trees.*—12,100 lbs. (2014), 11,000 lbs. (2015), 16,500 lbs. (2016).

Disease resistance/susceptibility: Similar to 'Bosc'.
Market use: Fresh, dessert.
Storage characteristics: Excellent.

I claim:

1. A new and distinct pear tree substantially as described and illustrated herein.

* * * * *